United States Patent [19]

Bergman et al.

[11] 4,328,164
[45] May 4, 1982

[54] COBALT ALKYLNITROSO COMPLEXES AND METHODS THEREWITH

[75] Inventors: Robert G. Bergman, Kensington; Paul N. Becker, Berkeley, both of Calif.; Mary A. White, Schenectady, N.Y.

[73] Assignee: The Regents of the University of California, Berkeley, Calif.

[21] Appl. No.: 177,495

[22] Filed: Aug. 12, 1980

[51] Int. Cl.$^3$ .............................................. C07F 15/06
[52] U.S. Cl. .............................................. 260/439 CY
[58] Field of Search .................................. 260/439 CY

[56] References Cited

U.S. PATENT DOCUMENTS

| | | | |
|---|---|---|---|
| 2,865,707 | 12/1958 | Hogsed | 260/439 R X |
| 3,086,036 | 4/1963 | Coffield et al. | 260/439 CY |
| 3,088,960 | 5/1963 | Wollensak | 260/439 CY |
| 3,361,777 | 1/1968 | King | 260/439 CY |
| 3,657,297 | 4/1972 | Spicer et al. | 260/439 CY |

OTHER PUBLICATIONS

Brunner et al., Angew. Chem. Internat. Edit. 10, pp. 515–516, (1971).
Brunner et al., J. Organometal. Chem. 61, 401–414, (1973).
Brunner, J. Organometal. Chem. 12, 517–522, (1968).
Evard et al., J. Organometal. Chem. 124, 59–70, (1977).
Chong et al., J. Amer. Chem. Soc. 99, 3420–3426, (1977).
Backvall, Tet. Let. 2, 163–166, (1978).
Barluenga et al., Synthesis, pp. 962–964, (1979).
Aranda et al., Synthesis, 504, (1974).
Fieser & Fieser, Reagents For Organic Synthesis V2, p. 584, (1967).

*Primary Examiner*—Helen M. S. Sneed
*Attorney, Agent, or Firm*—Phillips, Moore, Lempio & Majestic

[57] ABSTRACT

This invention provides a general method for the conversion of alkenes to primary vicinal diamines by use of a cobalt alkylnitroso complex and reduction with lithium aluminum hydride. A preferred species has the structure

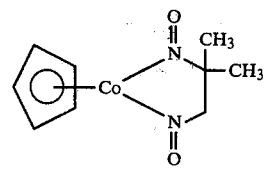

2 Claims, No Drawings

COBALT ALKYLNITROSO COMPLEXES AND METHODS THEREWITH

FIELD OF THE INVENTION

This invention relates generally to a reagent for aminating alkenes, and more particularly to a cobalt alkylnitroso complex useful for converting alkenes to primary vicinal diamines.

The invention described herein was made in the course of, or under, a grant from the National Institutes of Health.

PRIOR ART

Vicinal diamines are useful precursors in many syntheses of practical application. In pharmaceutical applications, vicinal diamine precursors are useful to synthesize various biologically active compounds. For example, Biotin may be synthesized from a diamine precursor of the structure

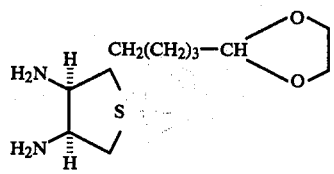

by conversion of the vicinal, primary amino groups to a cyclic urea structure as an intermediate compound.

Vicinal diamines are also used in preparing various types of polymers and in preparing chelating agents, for example from diamine precursors such as

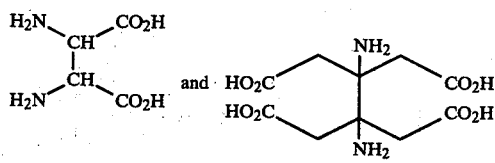

It is particularly desirable for many syntheses that vicinal diamines have primary diamino groups, since derivatives are more easily formed therefrom than with secondary or tertiary amines.

Several reagents have been developed in the last decade for the conversion of various specific olefins to diamines. These reagents have not been suitable for converting a variety of olefins to diamines, or have not produced primary vicinal diamines. It has been reported by Brunner and Loskot, *Agnew. Chem. Internat. Edit.* 10,515(1971) and *J. Organonet. Chem.* 61,401(1973), that a cobalt nitrosyl dimer of the structure

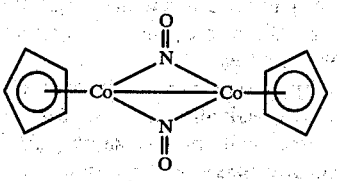

reacts in the presence of NO with norbornene to give a complex of the structure

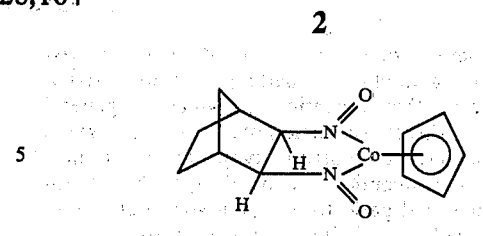

It was noted that the above complex appeared to react with both LiAlH$_4$ and I$_2$; however, the products of these reactions were not reported.

Accordingly, a general, substantially direct method for the preparation of primary vicinal diamines has hitherto been lacking. Additionally, for applications such as synthesizing biologically active compounds, it is desirable that the vicinal diamine precursor be of substantially one stereoisometric form. Biotin, for example, requires a cis primary diamine precursor.

SUMMARY OF THE INVENTION

It is an object of the present invention to provide a stable reagent useful for converting a variety of alkenes to primary diamines having adjacent amino groups.

It is a further object of the present invention to provide a method for preparing a diamine compound having primary adjacent amino groups in good to excellent isolated yields.

It is yet another object of the present invention to provide a method for preparing a diamine compound having primary adjacent amino groups and a plurality of stereoisomers to yield a reaction product of at least about 65% of one of the stereoisomers.

In one aspect of the present invention, a compound is provided which has the structure

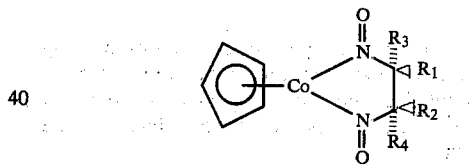

wherein R$_1$ is phenyl, hydrogen or alkyl, R$_2$ is phenyl, hydrogen or alkyl, R$_3$ is phenyl, hydrogen or alkyl and R$_4$ is phenyl, hydrogen or alkyl.

In another aspect of the present invention, a method for preparing a diamine compound having primary adjacent amino groups comprises the steps of providing a reagent of the above-described structure and contacting the reagent with LiAlH$_4$ to form the diamine compound.

In a further aspect of the present invention a method for aminating a compound having a carbon-carbon double bond to prepare a diamine product compound comprises admixing a reaction mixture consisting essentially of a reagent of the structure

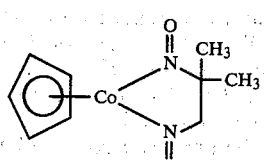

and the compound having the carbon-carbon double bond, the reagent reacting with the compound to form an adduct compound, and contacting the reaction mixture having the adduct compound therein with LiAlH₄.

Accordingly, this invention provides a general method for the direct conversion of a variety of alkenes by utilizing a cobalt alkylnitroso complex in accordance with the present invention. Yields of up to 90% of diamine product, and good to excellent stereoselectivity may be obtained in accordance with the present invention.

Additional objects, advantages and novel features of the invention will be set forth in part in the description which follows, and in part will become apparent to those skilled in the art upon examination of the following description or as may be learned by practice of the invention.

DETAILED DESCRIPTION OF THE INVENTION

The present invention provides novel precursor compounds which may be readily reduced to diamine compounds having primary adjacent amino groups thereon. These novel compounds shall first be described, and the method aspects of the present invention shall then be described.

COMPOUNDS

The novel compounds of the present invention are of the general structure illustrated by Formula 1, below.

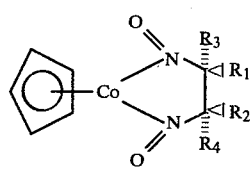

Formula 1

A compound of the general structure as represented by Formula 1, above, shall hereinafter be sometimes referred to as a cobalt alkylnitroso complex. These cobalt alkylnitroso complexes are prepared from alkenes of the general structure

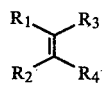

The $R_1$, $R_2$, $R_3$ and $R_4$ substituents of the cobalt alkyl nitroso complexes derive from and are the same as the $R_1$, $R_2$, $R_3$ and $R_4$ groups of the alkene chosen to prepare each one of the cobalt alkylnitroso complexes.

These alkenes can be terminal, E- and Z- di-, tri- and tetrasubstituted alkenes. More particularly, $R_1$ may be phenyl, hydrogen or alkyl, $R_2$ may be phenyl, hydrogen or alkyl, $R_3$ may be phenyl, hydrogen or alkyl and $R_4$ may be phenyl, hydrogen or alkyl.

By alkyl is meant saturated carbon chains which may be unsubstituted or which may be substituted with various known organic functional groups such as, for example, hydroxyl. The carbon chain of these alkyl groups may be branched or non-branched. The carbon chain of these alkyls can be of various lengths, although an upper limit on the length, if the diamine compound to be prepared from the precursor cobalt alkyl nitroso complex is to be purified by distillation, is about $C_{10}$. This is because diamine compounds having $R_1$, $R_2$, $R_3$ and/or $R_4$ as alkyls of chain length greater than about 10 have low volatility. However, longer carbon chain lengths are feasible in accordance with the present invention where the diamine compound is not isolated, or is purified by conversion to various derivatives, such as cyclic urea derivatives.

A particularly preferred one of the cobalt alkylnitroso complexes is illustrated by Formula 2, below.

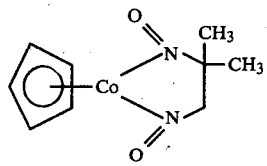

Formula 2

The Formula 2 compound shall be hereinafter sometimes referred to as the dimethyl species, and aspects and particular advantages thereof shall be further discussed hereinafter.

Preparations of the cobalt alkylnitroso complexes are generally illustrated by reaction scheme I, below. "Cp" stands for

Reaction Scheme I

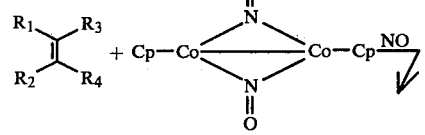

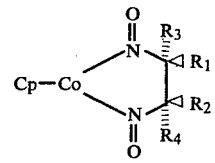

Reaction Scheme I, above, illustrates the reaction of a cobalt nitrosyl dimer with alkene and NO. The cobalt nitrosyl dimer is known and may be prepared, for example, by the method of H. Brunner, *J. Organonet. Chem.* 12,517(1968).

The mechanism of Reaction Scheme I is believed to proceed by means of an initially-formed intermediate CpCo (NO)₂.

A cobalt alkylnitroso complex formed as in Reaction Scheme I is preferably stabilized by performing the reaction at about 0° C. The cobalt alkylnitroso complexes may be isolated following Reaction Scheme I, or may be directly utilized in solution (e.g., without isolation) to prepare diamine compounds, as shall be hereinafter further described.

The dimethyl species is a particularly preferred one of the inventive cobalt alkylnitroso complexes due to its excellent thermal stability and stability in air, and also due to certain advantages when used to prepare diamine compounds, which use and advantages shall be further described.

Example I, below, illustrates the preparation and analysis of the preferred dimethyl species.

EXAMPLE I (3,3 dimethyl species)

Under an inert atmosphere ($N_2$), 0.932 g (3.0 m moles) of cobalt nitrosyl dimer was weighed into a reaction flask. Dry, oxygen-free $CH_2Cl_2$ (17 mL.) was added and the mixture was cooled to 0° C. in an ice bath. Argon was bubbled through the mixture for three minutes. Isobutylene and nitric oxide gases were allowed to purge their separate tubings before being bubbled through the reaction solution. Both gases were simultaneously bubbled very slowly (about 3 mL/min for each gas) through the reaction solution. The disappearance of cobalt nitrosyl dimer was followed by TLC on silica gel.

After 70 minutes, the solution was degassed for five minutes by bubbling with argon to remove excess NO and flash chromotographed on silica gel using 5% ether/$CH_2Cl_2$ as eluant and argon as the pressure source. The dimethyl species eluted as a dark red band. The eluted red solution was evaporated and redissolved in a small quantity of $CH_2Cl_2$ followed by the addition of ether (9 mL) and slow cooling to −60° C. Yield after filtration and drying under vacuum was 0.895 g (3.7 m moles), or 62% with respect to the cobalt nitrosyl dimer. The dimethyl species was obtained as black crystals and analyzed.

Analysis

H-nmr ($C_6D_6$): 4.75 (s,5H), 2.47 (s,2H), 1.01 (s,6H)ppm.

IR (KBr): 1420 (m), 1361 (m), 1351(s), 1310 (m) $cm^{-1}$.

Anal. Calcd. for $C_8H_{13}N_2O_2Co$: C, 45.01; H, 5.46; N, 11.67; Co, 24.5. Found: C, 45.03; H, 5.46; N, 11.72; Co, 24.0.

Example II, below, further illustrates preparation of a cobalt alkylnitroso complex of the present invention wherein the alkene was trans-3-hexene.

EXAMPLE II (3,4 diethyl species)

A 3-neck 25 ml pear-shaped flask equipped with stir bar, rubber septum, gas inlet bubbler, and dry ice condenser was charged with 0.765 g (2.49 mmol) of the cobalt nitrosyl dimer, [CpCoNO]$_2$ under a positive pressure of argon. Freshly distilled, oxygen-free THF (10 ml) was added via cannula and 423 microliters (3.37 mmoles) of degassed trans-3-hexene was added via syringe. The resulting dark green solution was cooled to 0° C. in an ice bath and the condenser cooled to −78° C. to prevent loss of the olefin by evaporation. Argon was bubbled through the mixture for 10 min. Nitric oxide gas was then allowed to purge the tubing before being bubbled through the solution. The gas was bubbled very slowly (3 ml/min) through the reaction mixture. The disappearance of trans-3-hexene was monitored by GC, and the disappearance of [CpCoNO]$_2$ was followed by TLC on silica gel.

A number of different alkenes were utilized to prepare various cobalt nitroso complexes. Such preparations were by procedures analogous to Examples I and II, above. Data from preparation of seven cobalt nitroso complexes are summarized in Example III, below.

Example III

| | Alkene | Mmoles alkene | Mmoles [CpCoNO]$_2$ | $\nu$No of Complex ($cm^{-1}$) | Reaction Time (min) |
|---|---|---|---|---|---|
| (1) | Ph, H / C=C / $CH_3$, $CH_3$ | 3.35 | 2.50 | 1356, 1387 1430 | 120 |
| (2) | $CH_3$, $CH_3$ / C=C / $CH_3$, $CH_3$ | 3.35 | 2.50 | 1358, 1388 1435, 1434 | 85 |
| (3) | $CH_3CH_2$, H / C=C / H, $CH_2CH_3$ | 2.90 | 2.20 | 1362 1427 | 75 |
| (4) | $CH_3CH_2$, H / C=C / $CH_2CH_3$, H | 3.30 | 2.49 | 1370 1418 | 150 |
| (5) | $C_4H_9CH=CH_2$ | 3.33 | 2.48 | 1370 1427 | 60 |
| (6) | Ph, H / C=C / H, $CH_3$ | 3.35 | 2.53 | 1359, 1371 1428 | 90 |
| (7) | Ph, H / C=C / $CH_3$, H | 3.30 | 2.47 | 1354, 1378 1428 | 120 |

METHODS

In accordance with the present invention, a method for preparing a diamine compound having adjacent primary amino groups comprises the steps of providing a cobalt alkyl nitroso complex, such as has been previously described, as a reagent and contacting the cobalt alkyl nitroso complex with lithium aluminum hydride to form the diamine compound as a reaction product. The inventive method is generally illustrated by Reaction Scheme II as follows.

Reaction Scheme II

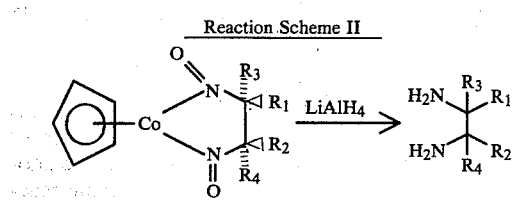

Wherein $R_1$, $R_2$, $R_3$ and $R_4$ are as previously described.

The cobalt alkylnitroso complex of the providing step is normally in solution of a suitable organic solvent, for example tetrahydrofuran. The lithium aluminum hydride of the contacting step is normally suspended in the same liquid solvent.

The cobalt alkylnitroso complex may be freshly prepared by dissolving or diluting in solvent, or may be a solution as results from Reaction Scheme I. That is, the cobalt nitroso complexes formed as previously discussed and illustrated by Reaction Scheme I need not be isolated, but may be directly utilized for preparing the diamine compounds as illustrated in Reaction Scheme II, with good to excellent overall yield of the reaction product diamine compound.

It is preferred that the contacting step be conducted at a temperature less than about 0° C., as it has been found that depressing the temperature during the contacting step assists in stabilizing the cobalt alkyl nitroso complexes in solution. More preferably, the temperature during the contacting step is from about −50° C. to about −70° C., and most preferably, the contacting step includes adding the solution having the cobalt nitroso complex therein to a liquid suspension of lithium aluminum hydride at a temperature of between about −50° C. to about −70° C. with rapid stirring.

Example IV, below, illustrates the inventive method.

EXAMPLE IV

A solution of the diethyl species was prepared by the procedure described in Example II, above. This reagent solution was then degassed for five minutes by bubbling with argon to remove excess NO. The reagent solution was diluted to a total volume of 20 ml with THF (added via cannula), and cooled to −65° C. The resulting dark red reagent solution was added dropwise, via cannula, over a 15-minute period to a 250 ml 3-neck round bottom flask fitted with a reflex condenser and rubber septum, and containing 1.70 g (42.6 mmoles) of LiAlH$_4$ magnetically stirred in 50 ml of THF at −70° C. under a nitrogen atmosphere. The red reaction mixture became dark green in color, as the temperature rose to between −55° and −60° C. The initial reaction vessel was rinsed with 20 ml of THF and added in the same manner to the LiAlH$_4$ mixture. The dry ice bath was allowed to warm to room temperature and the solution was stirred for a total of 18 hours. The mixture was brought to reflux for one hour, then cooled to −60° C. and the excess LiAlH$_4$ destroyed by sequential dropwise addition of 1.70 ml H$_2$O, 1.70 ml 15% NaOH, and 5.10 ml H$_2$O. After warming to room temperature and stirring for four hours, the mixture was filtered and the precipitate washed with 2×30 ml of THF. The filtrate was dried over K$_2$CO$_3$, filtered, and the solvent removed under vacuum to give dark yellow oil. This was distilled under reduced pressure at <5μ and room temperature into a liquid nitrogen cooled trap yielding 0.232 g of reaction product diamine compound (60% overall yield with respect to original, trans-3-hexene) of a clear, pale yellow oil that was 98% pure by GC, IR and $^1$H-NMR. Removal of the minor impurities by preparative GC gave analytically pure diamine.

The tabulated data of Example V, below, illustrates the inventive method with the seven solutions of cobalt nitroso complexes from Example III. Each of these seven solutions was contacted with LiAlH$_4$ in an analogous manner to Example IV to form the diamine reaction product.

EXAMPLE V

| Cobalt Nitroso Complex | Diamine Reaction Product Yield % | Ratio of Diastereomers |
|---|---|---|
| (1) | 78* | — |
| (2) | 66* | — |
| (3) | 80 | 90:10** |
| (4) | 62 | 34:66** |
| (5) | 79 | — |
| (6) | 90 | 85:15** |
| (7) | 74* | 28:72** |

*Yield of diamine reaction product isolated after conversion to cyclic urea derivative.
**Threo:erythro As may be seen from Example V, above, adding the solution having the cobalt nitroso complex as reagent therein to the suspension of lithium aluminum hydride with rapid stirring at temperatures of between about −50° C. to about −70° C. is preferred for the contacting step where the reaction product diamine compound has a plurality of stereoisomers.

In a further aspect of the present invention, a method is provided for diaminating a compound having a carbon-carbon double bond to prepare a diamine compound having adjacent primary amino groups. The method comprises the steps of admixing a reaction mixture consisting essentially of two reactants to form an adduct compound in the reaction mixture. The reaction mixture is then contacted with lithium aluminum hydride to form the desired diamine product.

One of the two reactants of the admixing step is the preferred dimethyl species of the cobalt alkyl nitroso compound, e.g., the compound whose structure is illustrated by FIG. 2. The other of the two reactants is the compound having the carbon-carbon double bond which is to be diaminated. The dimethyl species, or reagent, reacts with this compound by adding at the carbon-carbon double bond to form an adduct compound in the reaction mixture.

A wide variety of compounds may be diaminated by practice of the inventive method. For example, bicyclic, cyclic and linear alkenes may be diaminated, and such alkenes may include various functional moieties such as, for example, hydroxyl groups. Additionally, the compound to be aminated may be a non-homocyclic compound, for example such as butadiene sulfone (which would normally be reduced to sulfide in the LiAlH$_4$ step) or a derivative thereof, so long as the compound to be aminated has a carbon-carbon double bond at which the reagent will add to form the adduct compound.

As has been already noted, the dimethyl species is quite stable. Thus the dimethyl species may be bottled, shipped and stored in crystalline form until its use is desired as reagent in the diaminating method. The dimethyl species also provides that the admixing step needs no NO for forming the adduct compound, and that the isobutylene concurrently formed with the adduct compound in the reaction mixture volatilizes from the reaction mixture, so that the reaction mixture during the contacting step consists essentially of the solubilized adduct compound. Thus, yield and isolation of the diamine compound following reduction with lithium aluminum hydride is facilitated.

Example VI, below, illustrates the diaminating method.

EXAMPLE VI

(a) Formation of Adduct Compound

Freshly chromatographed dimethyl species (prepared from 0.268 g (0.87 mmoles) of cobalt nitrosyl dimer and isobutylene as in Example I, above) was dissolved in 25 ml benzene in a 2-neck 50 ml round bottom flask equipped with a stir bar, reflux condenser and rubber septum. Norbornylene (1.64 g, 17.4 mmoles) was added and the mixture was degassed with argon via syringe, and heated to reflux using a heating mantle. The reaction was followed by TLC on reverse phase-8 with 5% $H_2O/CH_3CN$ as developer. After two hours, the solvent was removed on a rotary evaporator and the black powder that remained was dried under vacuum. The yield was 0.364 g (1.3 mmoles; 75% based on the dimethyl species) of norbornylene adduct compound which was identified by comparison of its $^1$H-nmr spectrum in benzene-$d_6$ with that of a sample prepared by the reaction of the cobalt nitrosyl dimer with norbornylene and NO.

(b) Formation of Diamine Compound

The adduct compound of subpart (a), above, was divided into two samples, each was dissolved in THF, and then treated as follows. The first sample was added to a suspension of lithium aluminum hydride in tetrahydrofuran with rapid stirring at a temperature of 0° C. On refluxing the tetrahydrofuran, the cis-exo isomer made up 84% of the reaction product. The second sample was added to a suspension of lithium aluminum hydride at −65° C., which gave a reaction product diamine having 90% of the cis-exo isomer.

The reactions of Example VI are generally illustrated by Reaction Scheme IV, below.

Reaction Scheme IV

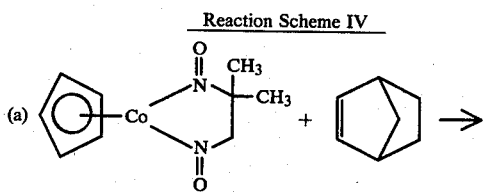

-continued
Reaction Scheme IV

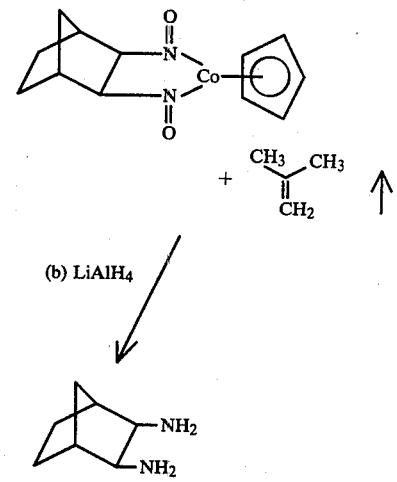

We claim:

1. A compound of the structure

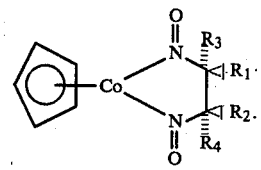

wherein $R_1$ is phenyl, hydrogen or alkyl, $R_2$ is phenyl, hydrogen or alkyl, $R_3$ is phenyl, hydrogen or alkyl and $R_4$ is phenyl, hydrogen or alkyl, and at least one of $R_1$, $R_2$, $R_3$ and $R_4$ is phenyl or alkyl.

2. The compound

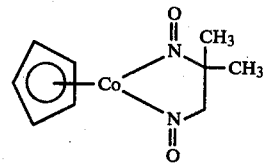

* * * * *